(12) United States Patent
Horowitz

(10) Patent No.: US 9,060,174 B2
(45) Date of Patent: Jun. 16, 2015

(54) METHOD AND SYSTEM FOR SELECTIVELY BREAKING PREDICTION IN VIDEO CODING

(75) Inventor: Michael Horowitz, Austin, TX (US)

(73) Assignee: Fish Dive, Inc., Palo Alto, CA (US)

( * ) Notice: Subject to any disclaimer, the term of this patent is extended or adjusted under 35 U.S.C. 154(b) by 479 days.

(21) Appl. No.: 13/336,475

(22) Filed: Dec. 23, 2011

(65) Prior Publication Data

US 2012/0163452 A1 Jun. 28, 2012

Related U.S. Application Data

(60) Provisional application No. 61/427,569, filed on Dec. 28, 2010.

(51) Int. Cl.
| H04N 7/12 | (2006.01) |
| H04N 19/436 | (2014.01) |
| H04N 19/105 | (2014.01) |
| H04N 19/70 | (2014.01) |
| H04N 19/46 | (2014.01) |
| H04N 19/61 | (2014.01) |
| H04N 19/117 | (2014.01) |
| H04N 19/174 | (2014.01) |
| H04N 19/82 | (2014.01) |

(52) U.S. Cl.
CPC .......... *H04N 19/436* (2014.11); *H04N 19/105* (2014.11); *H04N 19/70* (2014.11); *H04N 19/46* (2014.11); *H04N 19/61* (2014.11); *H04N 19/117* (2014.11); *H04N 19/174* (2014.11); *H04N 19/82* (2014.11)

(58) Field of Classification Search
USPC ........................................ 375/240.01–240.29
See application file for complete search history.

(56) References Cited

U.S. PATENT DOCUMENTS

| 6,263,023 | B1 | 7/2001 | Ngai | |
| 7,162,093 | B2 * | 1/2007 | Regunathan et al. | 382/233 |
| 2005/0008240 | A1 | 1/2005 | Banerji et al. | |
| 2005/0141620 | A1 * | 6/2005 | Hattori | 375/240.25 |
| 2005/0286634 | A1 | 12/2005 | Duvivier | |
| 2006/0115001 | A1 | 6/2006 | Wang et al. | |
| 2007/0104269 | A1 | 5/2007 | Xue et al. | |
| 2008/0219349 | A1 | 9/2008 | Huang et al. | |
| 2009/0010334 | A1 | 1/2009 | Ueda et al. | |
| 2009/0323809 | A1 * | 12/2009 | Raveendran | 375/240.16 |
| 2010/0128803 | A1 * | 5/2010 | Divorra Escoda et al. | 375/240.29 |
| 2010/0158401 | A1 | 6/2010 | Shiraishi et al. | |

(Continued)

OTHER PUBLICATIONS

International Bureau of WIPO, International Search Report and Written Opinion of the International Searching Authority dated Apr. 17, 2012, issued in respect of International Application No. PCT/CA2011/001412.

(Continued)

*Primary Examiner* — Gims Philippe
(74) *Attorney, Agent, or Firm* — Fish & Richardson P.C.

(57) ABSTRACT

Described are techniques in video coding and/or decoding that allow for selectively breaking prediction and/or in loop filtering across segment boundaries between different segments of a video picture. A high layer syntax element, such as a parameter set or a slice header, may contain one or more indications signalling to an encoder and/or decoder whether an associated prediction or loop filtering tool may be applied across the segment boundary. In response to such one or more indications, the encoder and/or decoder may then control the prediction or loop filtering tool accordingly.

16 Claims, 8 Drawing Sheets

(56) References Cited

U.S. PATENT DOCUMENTS

| | | | |
|---|---|---|---|
| 2010/0189181 A1 | 7/2010 | Zheng et al. | |
| 2010/0296585 A1 | 11/2010 | Matsuura | |
| 2010/0303153 A1* | 12/2010 | Kadono | 375/240.13 |
| 2012/0082244 A1* | 4/2012 | Chen et al. | 375/240.29 |
| 2012/0163453 A1 | 6/2012 | Horowitz | |

OTHER PUBLICATIONS

Dhont et al.; Flexible macroblock ordering as a content adaptation tool in H.264/AVC; Proceedings of the SPIE, vol. 6015, pp. 601506-1-601506-9; Oct. 24, 2005.

International Preliminary Report on Patentability in International Application No. PCT/CA2011/001412, dated Jul. 2, 2013, 7 pages.

International Bureau of WIPO, International Search Report and Written Opinion of International Searching Authority dated Mar. 20, 2012, issued in respect of International Application No. PCT/CA2011/001411, 8 pages.

International Preliminary Report on Patentability in International Application No. PCT/CA2011/001411, dated Jul. 2, 2013, 5 pages.

Bossen, "Common test conditions and software reference configurations," JCT-VC Document JCTVC-B300, Geneva, Jul. 2010, 12 pages.

ITU-T Recommendation H.263 version 2 (H.263+), "Video coding for low bit rate communication," 1998, 167 pages.

ITU-T Recommendation H.264 and ISO/IEC 14496-10, "Advanced Video Coding for Generic Audiovisual Services," (Mar. 2010), 676 pages.

JCT-VC, "Test Model under Consideration Software 0.9-ahg-slices," retrieved on Dec. 11, 2014, retrieved from the Internet: URL: https://hevc.hhi.fraunhofer.de/svn/svn_HEVCSoftware/branches/0.9-ahg-slices/, 1 page.

Misra et al., "Entropy slices for parallel entropy coding," JCT-VC Document, JCTVC-C256, Guangzhou, Oct. 2010, 6 pages.

Sjoberg and Wennersten, "Fine granularity slices," JCT-VC Document, JCTVC-C154, Guangzhou, Oct. 2010, 4 pages.

Sullivan et al., "Overview of the High Efficiency Video Coding (HEVC) Standard," IEEE Transactions on Circuits and Systems for Video Technology, Dec. 2012, 22(12):1649-1668.

Wenger and Horowitz, "Flexible Macroblock ordering (FMO)," JVT-0089, May 2002, 22 pages.

Zhou, "Sub-picture based raster scanning coding order for HEVC UHD video coding," JCTVC-B062, Geneva, Jul. 2010, 4 pages.

* cited by examiner

METHOD AND SYSTEM FOR SELECTIVELY BREAKING PREDICTION IN VIDEO CODING

CROSS-REFERENCE TO RELATED APPLICATIONS

This application claims priority from U.S. Provisional Patent Application Ser. No. 61/427,569, filed Dec. 28, 2010, entitled "PICTURE SEGMENTATION USING GENERALIZED SLICES", the entire contents of which are incorporated herein by reference.

FIELD

Embodiments of the invention relate to video compression, and more specifically, to the selective use of prediction and in-loop filtering mechanisms at picture segment boundaries of video pictures.

BACKGROUND

Digital video capabilities can be incorporated into a wide range of devices, including digital televisions, digital direct broadcast systems, wireless broadcast systems, personal digital assistants (PDAs), laptop or desktop computers, video cameras, digital recording devices, video gaming devices, video game consoles, cellular or satellite radio telephones, and the like. Digital video devices may implement video compression techniques, such as those described in standards like MPEG-2, MPEG-4, both available from the International Organization for Standardization ("ISO") 1, ch. de la Voie-Creuse, Case postale 56, CH-1211 Geneva 20, Switzerland, or www.iso.org, or ITU-T H.264/MPEG-4, Part 10, Advanced Video Coding ("AVC"), available from the International Telecommunication Union ("ITU"), Place de Nations, CH-1211 Geneva 20, Switzerland or www.itu.int, each of which is incorporated herein by reference in their entirety, or according to other standard or non-standard specifications, to encode and/or decode digital video information efficiently. Still other compression techniques may be developed in the future or are presently under development. For example, a new video compression standard known as HEVC/H.265 is under development in the JCT-VC committee. The HEVC/H.265 working draft is set out in "Wiegand et. al., "WD3: Working Draft 3 of High-Efficiency Video Coding, JCTVC-E603" March 2011, henceforth referred to as "WD3" and incorporated herein by reference in its entirety.

A video encoder can receive uncoded video information for processing in any suitable format, which may be a digital format conforming to ITU-R BT 601 (available from the International Telecommunications Union, Place des Nations, 1211 Geneva 20, Switzerland, www.itu.int, and which is incorporated herein by reference in its entirety) or in some other digital format. The uncoded video may be organized both spatially into pixel values arranged in one or more two-dimensional matrices as well as temporally into a series of uncoded pictures, with each uncoded picture comprising one or more of the above-mentioned two-dimensional matrices of pixel values. Further, each pixel may comprise a number of separate components used to represent color in digital format. One common format for uncoded video that is input to a video encoder has, for each group of four pixels, four luminance samples which contain information regarding the brightness/lightness or darkness of the pixels, and two chrominance samples which contain color information (e.g., YCrCb 4:2:0).

One function of video encoders is to translate (more generally "transform") uncoded pictures into a bitstream, packet stream, NAL unit stream, or other suitable transmission format (all referred to as "bitstream" henceforth), with goals such as reducing the amount of redundancy encoded into the bitstream to thereby increase transmission rates, increasing the resilience of the bitstream to suppress bit errors or packet erasures that may occur during transmission (collectively known as "error resilience"), or other application-specific goals. Embodiments of the present invention provide for at least one of the removal or reduction of redundancy, the increase in error resilience, and implementability of video encoders and/or associated decoders in parallel processing architectures.

One function of video decoders is to receive as its input a coded video in the form of a bitstream that may have been produced by a video encoder conforming to the same video compression standard. The video encoder then translates (more generally "transforms") the received coded bitstream into uncoded video information that may be displayed, stored, or otherwise handled.

Both video encoders and video decoders may be implemented using hardware and/or software conFIG.urations, including combinations of both hardware and software. Implementations of either or both may include the use of programmable hardware components such as general purpose central processing units (CPUs), such as found in personal computers (PCs), embedded processors, graphic card processors, digital signal processors (DSPs), field programmable gate arrays (FPGAs), or others. To implement at least parts of the video encoding or decoding, instructions may be needed, and those instructions may be stored and distributed using one or more non-transitory computer readable media. Computer readable media choices include compact disc read-only memory (CD-ROM), digital videodisc read-only memory (DVD-ROM), memory stick, embedded ROM, or others.

Video compression and decompression refer to certain operations performed in a video encoder and/or decoder. A video decoder may perform all, or a subset of, the inverse operations of the encoding operations. Unless otherwise noted, techniques of video encoding described herein are intended also to encompass the inverse of the described video encoding techniques (namely associated video decoding techniques).

The uncompressed, digital representation of video can be viewed as a sample stream, wherein the samples can be processed by the video display in scan order. One type of boundary often occurring in this sample stream is the boundary between pictures in the sample stream. Many video compression standards recognize this boundary and often divide the coded bitstream at these boundaries, for example, through the insertion of a picture header or other metadata at the beginning of each uncoded picture. Other boundaries that may occur in the sample stream include slice and tile boundaries, which may occur within an uncoded picture, as described below.

Prediction in video coding can occur at many levels.

One level is referred to henceforth as the "entropy coding level" and the prediction at that level is referred to as "encoding prediction". In this level, the decoding of an entropy coded symbol may require the successful decoding of previous entropy coded symbols. All or nearly all current video compression standards break the encoding prediction at both the picture and the slice level. That is, at the detection of a picture or slice header in the bitstream (or equivalent), the entropy coding related states used in the entropy coding are reset to an initialization state. One example for entropy coded prediction is the reset of CABAC states in ITU-T Rec. H.264.

Further, there can be coding mechanisms that do not fall into the common understanding of entropy coding related prediction, as defined above, but which are still related to the reconstruction control information associated with the bitstream, rather than pixel values. As an example, even some older standards such as the ITU-T Rec. H.261 standard allow coding of motion vectors as relative to one or more previously coded motion vectors. The detection of a group-of-blocks (GOB), slice or picture header resets this prediction vector to (0, 0).

There are also prediction mechanisms that span multiple pictures. For example, motion compensation can use (possibly motion compensated) pixel values from one or more reference pictures for prediction. This type of prediction is broken through the macroblock type (or equivalent). For example, intra macroblocks do not generally use prediction from reference pictures, whereas inter macroblocks may. Intra and Inter slices, in this sense, are simply accumulations of macroblocks belonging to those different macroblock types.

There are also prediction levels that include prediction based on pixel values that have already been reconstructed during the reconstruction process of the picture being encoded. One example is intra prediction mechanisms, such as the ones described in Annex I of ITU-T Rec. H.263. (Similar mechanisms are available in other video coding standards as well.)

In addition to prediction mechanisms, several video coding standards specify filters for performing in-loop filtering. One example is the in-loop filter specified in Annex J of ITU-T Rec. H.263.

For some applications, it may be advantageous to segment the picture being encoded into smaller data blocks, which segmenting can occur prior to, or during, the encoding. Two use cases for which picture segmentation may be advantageous are described below.

The first such use case involves parallel processing. Previously, standard definition video (e.g., 720×480 or 720×576 pixels) was the largest format in widespread commercial use. More recently HD (up to 1920×1080 pixels) formats as well as 4 k (4096×2048 pixels), 8 k (8192×4096 pixels), and still larger formats are emerging and finding use in a variety of application spaces. Despite the increase in affordable computing power over the years, as a result of the very large picture sizes associated with some of these newer and larger formats, it is often advantageous to leverage the efficiency of parallel processing to the encoding and decoding processes. Parallel encoding and decoding may occur, for example, at the instruction level (e.g., using SIMD), in a pipeline where several video coding units may be processed at different stages simultaneously, or on a large structure basis where collections of video coding sub units are processed by separate computing engines as separate entities (e.g., a multi-core general purpose processor). The last form of parallel processing can require picture segmentation.

The second such use case involves picture segmentation so as to create a bitstream suitable for efficient transport over packet networks. Codecs whose coded video is transported over IP and other packet networks can be subject to a maximum transmission unit ("MTU") size constraint. It is sometimes advantageous for the coded slice size to be such that the resulting packet containing the coded slice is as close to the MTU size as possible without exceeding that size, so as to keep the payload/packetization overhead ratio high, while avoiding fragmentation (and the resulting higher loss probability) by the network.

The MTU size differs widely from network to network. For example, the MTU size of many Internet connections may be set by the smallest MTU size of network infrastructure commonly used on the Internet, which often corresponds to limitations in Ethernet and may be roughly 1500 bytes.

The number of bits in a coded picture depends on many factors such as the source picture's dimensions, the desired quality, the complexity of the content in terms of suitability for prediction, and other factors. However, even at moderate quality settings and content complexity, for sequences of HD resolution and above, the size of an average coded picture easily exceeds the MTU size. For example, a video conferencing encoder can require about 2 MBit/s to encode a 720p60 video sequence. This results in an average coded picture size of roughly 33333 bits or 4167 bytes, which is considerably more than the 1500 bytes of the Internet's MTU size. At higher resolutions, the average picture size increases to values significantly above the Internet's MTU size. Assuming a similar compression ratio as in the 720p60 example above, a 4096×2048 (4 k) video at 60 fps (4 kp60) may require over 300,000 bits, or 25 MTU-sized packets for each coded video picture.

In many previous video coding standards (for example, up to and including WD3), a picture segment (or, at least, one form of a picture segment) is known as a "slice". In the following description, any kind of (e.g., video coding based) picture fragmentation that breaks at least one form of in-picture prediction, in-loop filtering, or other coding mechanism, may be referred to generally as a "slice". As such, structures such as the Group Of Blocks ("GOB") in ITU.T Rec. H.261 or ITU Rec. H.263 (available from the ITU; see above for H.264), slices in H.264 or the MPEG family of standards, may each constitute a "slice" as this term is used herein throughout. However, fragmentation units of RFC3984 or data partitions of H.264 may not constitute a "slice", as this term is used herein throughout, because they subdivide the bitstream of a coded picture and do not break in-picture prediction, in-loop filtering or another coding mechanism.

Referring to FIG.. 1, shown is an example 100 of picture segmentation using slices. A picture 101 is broken into two scan order slices 102, 103. The slice boundary is shown as a boldface line 104. The first macroblock 105 of the second slice 103 has address 11. The corresponding bitstream 106 for transmitting the picture 101, for example, when generated using the H.264 standard, can contain one or more parameter sets 107 that do not contain information about the slice boundaries, followed by the slice headers 108, 110 and slice data 109,111 of the two slices 102, 103. The slice header 110 of the second slice 103 is shown enlarged. The dimensions of the uncoded slice 103, for example, are determined by a decoder by a combination of at least two factors. First, the slice header 110 contains the address of the first macroblock 105 of slice 103. Second, the end of the slice is determined, for example, by the detection of a new slice header in the bitstream or, in the depicted example, by the end of the coded picture in the bitstream 112, i.e., after macroblock 24. All macroblocks between the first macroblock and the end of the slice make up the slice. It is noted that scan order modifications, such as Flexible Macroblock Ordering of H.264, can change the number of macroblocks in the slice by creating gaps.

One advantage of using slices over media-unaware segmentation mechanisms, such as, for example, those provided by IP at the routing layer, is that slices are at least to a certain extent independently decodeable (as discussed below in more detail), by breaking certain types of prediction at the boundaries between slices. The loss of one slice therefore does not necessarily render the other slices of a coded picture unusable or un-decodeable. Depending on the implementation of a fragmentation mechanism, the loss of a fragment, in contrast, may well render many other fragments unusable because fragmentation, as this term is used herein throughout, does not break any form(s) of prediction.

WD4 (B. Bross et. al., "WD4: Working Draft 4 of High-Efficiency Video Coding", available from http://wftp3.itu.int/av-arch/jctvc-site/2011_07_F_Torino/) is a draft specification relating to a digital video coding standard in development, which may be referred to as High Efficiency Video Coding (HEVC) or H.265. In addition to slices, WD4 also includes a picture segmentation mechanism known as "Tiles". According to WD4, a source picture can be divided into rectangular units called tiles, such that each pixel of the source picture is part of a tile (other constraints may also apply). A tile is, therefore, a rectangular part of a picture. Tile boundaries are determined by coordinates available in high-level syntax structures, which are known in WD4 as parameter sets. Tiles are described in more detail below.

With the possible exception of inter picture prediction, each of the in-picture prediction mechanisms or coding mechanisms described above may be broken by the decoding of a picture header (or equivalent, such as the decoding of a slice with a frame number different from the previous slice). Whether those prediction mechanisms are broken across slice or tile boundaries depends on the video compression standard, and the type of slice in use.

In H.264, slices may be independently decodeable with respect to motion vector prediction, intra prediction, CA-VLC and CABAC states, and other aspects of the H.264 standard. Only inter picture prediction (including import of pixel data outside of the slice boundaries through motion compensation) is allowed. While this decoding independence increases error resilience, disallowing the aforementioned prediction across slice boundaries reduces coding efficiency.

In H.263, a video encoder has more flexibility in selecting which prediction mechanisms are broken through the use of slices or GOBs with non-empty GOB headers. For example, there is a bit included in the picture header, selectable when Annex R is in use, which signals to the decoder that no prediction or filtering at all occurs across slice/GOB (with non-empty headers) boundaries. Certain prediction mechanisms, such as motion vector prediction are broken across GOBs with non-empty headers and across slice boundaries, regardless of the state of Annex R. Others are controlled by Annex R. For example, if the bit is not set, motion vectors may point outside the spatial area co-located with the current slice/GOB with non-empty header in the reference picture(s), thereby potentially "importing" sample values that are used for motion compensation into the current slice from an area that is not inside of the geometric area of the slice/GOB in the reference picture. Further, unless Annex R is active, loop filtering may incorporate sample values outside of the slice/GOB. Similarly, there is another bit in the picture header that enables or disables Intra prediction.

However, in most standards, the decision of breaking in picture prediction is made at least at picture granularity, and in some cases at sequence granularity. In other words, using H.263 as an example, it is not possible to mix slices in a given picture that have the deblocking filter enabled or disabled (respectively), nor is it possible to enable/disable intra prediction at the slice level.

As already described, picture segmentation allows breaking a picture into spatial areas smaller than a whole picture. While the most common applications for picture segmentation, as described, appear to be MTU size matching and parallelization, picture segmentation can also be used for many other purposes, including those that adapt the segment size and shape to the content. Region of interest coding is one of several examples. In such cases, it is possible that certain parts of a picture can be more efficiently coded than others (in the sense that spending a lower number of bits for encoding yield comparable visual experience) when different coding tools, including different prediction mechanisms, are applied. For example, some content may benefit from deblocking filtering and may not respond well to intra prediction, whereas other content in the same picture may better be coded without deblocking filtering, but could benefit from intra prediction. A third content may best be coded with both deblocking filtering and intra prediction enabled. All this content can be located in the same picture when the picture is tiled, which occurs, for example, in interview situations, or in video conferencing.

One shortcoming of the existing mechanisms for prediction breaking at segment boundaries is that the enablement and/or disablement of the prediction breaking is generally hard-coded into the existing video coding standards, thereby making it difficult or impossible to selectively break prediction mechanisms at segment boundaries based, for example, on the characteristics of the content to be encoded.

A need therefore exists for an improved method and system to enable or disable, on a per slice basis, prediction and in-loop filtering mechanisms individually, or as a group. Accordingly, a solution that addresses, at least in part, the above and other shortcomings is desired.

Further, a need exists on a per picture (or group of pictures, sequences, etc.) basis to enable, or disable prediction mechanisms and/or in-loop filtering mechanisms across header-less (or equivalent) picture segment boundaries (such as tile boundaries) individually, or as a group. Accordingly, a solution that addresses, at least in part, the above and other shortcomings is desired.

SUMMARY

Embodiments of the present invention provide method(s) and system(s) for encoding and/or decoding video pictures in which a plurality of prediction and in-loop filtering tools for a picture segment may be selectively enabled or disabled.

According to one aspect of the invention, an encoder may indicate for one or more prediction tools whether that tool may take information from outside the picture segment currently being processed as reference information for processing within that picture segment. The encoder may provide such indication for a single prediction tool (for example, entropy prediction, intra prediction, motion compensated prediction, motion vector prediction, henceforth referred to as prediction tools) and/or a single filtering tool (for example, adaptive interpolation filtering, adaptive loop filtering, deblocking, filtering, sample adaptive offset, henceforth referred to as loop filter tools), as well as others. Alternatively, the encoder may provide such indication for a plurality of pre-defined tools or a predefined groups of tools that may include any of the above-noted prediction and loop filter tools, as well as others. Doing so may be useful in support of parallelization of encoders and decoders as well as for certain application scenarios such as soft continuous presence (stitching together coded pictures in the compressed domain).

According to an aspect of the invention, when header-less picture segmentation (such as tiles) is in use, the encoder may indicate to the prediction tool, loop filter tool, or plurality of pre-defined groups of tools, whether that tool may take information across horizontal, vertical, or both horizontal and vertical tile boundaries to be used as reference information.

In the particular case of H.264 or HEVC, as an example, the encoder may set values for "coding interrupt indication" flags used for prediction and in-loop filtering tools such as: intra prediction referencing sample values outside the slice/tile boundary; vectors referencing sample values outside the slice/tile boundary (i.e., through motion compensation); use of CABAC states outside the slice/tile boundary; use of CA-VLC states outside the slice/tile boundary; use of PIPE or similar V2V entropy coding states outside the slice/tile boundary (HEVC-only); and, use of states and sample values outside the slice/tile boundary of in-loop filters such as adaptive interpolation filters, adaptive loop filters, deblocking loop filters, or sample adaptive offset.

According to an aspect of the invention, the use or other enablement of coding tools may not be indicated in the form of flags, but through manipulation of other data structures, such as "coding interrupt indication" integers that may, in some cases, combine a plurality of the aforementioned flags, or preferred permutations of those flags, into a single symbol.

According to an aspect of the invention, the maximum length of a motion vector pointing outside of a slice boundary may be coded in an appropriate entropy coding representation of an integer, thereby indicating not only the non-use of motion compensation up to the distance allowed by the level in use, but also the maximum that is allowed, which can, for example, aid resource allocation in a decoder implementation.

According to an aspect of the invention, at least one of the aforementioned coding interrupt indication flags or other data coding interrupt indication structures may be stored in the slice header, picture header, parameter set, or equivalent.

According to an aspect to the invention, a decoder may react to the presence of the flags or other data structures by breaking the indicated prediction tools across slice/tile boundaries as opposed to other potentially suitable boundaries.

In one broad aspect, there is provided a method for decoding a coded video picture comprising a plurality of segments. The method may include, in respect of at least one segment of the coded video picture not having an associated segment header, obtaining from the coded video picture at least one indication of at least one prediction or in-loop filtering operation to be applied to the coded video picture, and controlling the at least one prediction or in-loop filtering operation in response to the at least one indication. In some cases, the coded video picture may contain at least two segments without an associated segment header.

In another broad aspect, there is provided a method for encoding a video picture comprising a plurality of segments. The method may include, in respect of at least one segment of the video picture not having an associated segment header, obtaining at least one indication of at least one prediction or in-loop filtering operation to be applied to the at least one segment not having an associated segment header, and controlling the at least one prediction or in-loop filtering operation during encoding of the video picture in response to the at least one indication. In some cases, the video picture may contain at least two segments without an associated segment header.

In yet another broad aspect, there is provided a non-transitory computer readable media having computer executable instructions stored thereon for programming one or more processors to perform a method of decoding a coded video picture comprising a plurality of segments. The method may include, in respect of at least one segment of the coded video picture not having an associated segment header, obtaining from the coded video picture at least one indication of at least one prediction or in-loop filtering operation to be applied to the coded video picture, and controlling the at least one prediction or in-loop filtering operation in response to the at least one indication. In some cases, the coded video picture may include at least two segments without an associated segment header.

In yet another broad aspect, there is provided a non-transitory computer readable media having computer executable instructions stored thereon for programming one or more processors to perform a method of encoding a video picture comprising a plurality of segments. The method may include, in respect of at least one segment of the video picture not having an associated segment header, obtaining at least one indication of at least one prediction or in-loop filtering operation to be applied to the at least one segment not having an associated segment header, and controlling the at least one prediction or in-loop filtering operation during encoding of the video picture in response to the at least one indication. In some cases, the video picture contains at least two segments without an associated segment header.

In yet another broad aspect, there is provided a data processing system that includes at least one of a processor and accelerator hardware conFIG.ured to execute a method of decoding a coded video picture comprising a plurality of segments. The method may include, in respect of at least one segment of the coded video picture not having an associated segment header, obtaining from the coded video picture at least one indication of at least one prediction or in-loop filtering operation to be applied to the coded video picture, and controlling the at least one prediction or in-loop filtering operation in response to the at least one indication. In some cases, the coded video picture contains at least two segments without an associated segment header.

In yet another broad aspect, there is provided a data processing system that includes at least one of a processor and accelerator hardware conFIG.ured to execute a method of encoding video picture comprising a plurality of segments. The method may include, in respect of at least one segment of the video picture not having an associated segment header, obtaining at least one indication of at least one prediction or in-loop filtering operation to be applied to the at least one segment not having an associated segment header, and controlling the at least one prediction or in-loop filtering operation during encoding of the video picture in response to the at least one indication. In some cases, the video picture contains at least two segments without an associated segment header.

In some embodiments, according to any of the above aspects, the at least one prediction or in-loop filtering operation may include at least one of entropy prediction, intra prediction, motion vector prediction, motion compensated prediction, adaptive loop filtering, adaptive interpolation filtering, deblocking filtering, or sample adaptive offset.

In some embodiments, according to any of the above aspects, the at least one of a plurality indications may be derived from at least one combination indications.

In some embodiments, according to any of the above aspects, the at least one indication may be coded as a vector indicative of the maximum length of a motion vector.

In some embodiments, according to any of the above aspects, the at least one indication may be coded in a parameter set.

In accordance with further aspects of the present invention, there is provided an apparatus such as a data processing system, a method for adapting this apparatus, as well as articles of manufacture such as a non-transitory computer readable medium or product having program instructions recorded and/or stored thereon for performing any of the methods described herein.

BRIEF DESCRIPTION OF THE DRAWINGS

Further features and advantages of the embodiments of the present invention will become apparent from the following detailed description, taken in combination with the appended drawings, in which.

It will be noted that throughout the appended drawings, like features are identified by like reference numerals.

DETAILED DESCRIPTION OF EMBODIMENTS

In the following description, details are set forth to provide an understanding of the invention. In some instances, certain software, circuits, structures and methods have not been described or shown in detail in order not to obscure the invention. The term "data processing system" is used herein to refer to any machine for processing data, including the computer systems, wireless devices, and network arrangements described herein. Embodiments of the present invention may be implemented in any computer programming language provided that the operating system of the data processing system provides the facilities that may support the requirements of these embodiments. Embodiments of the present invention may also be implemented in hardware or in a combination of hardware and software.

At least some embodiments of the present invention relate to selectively breaking prediction mechanisms and/or selectively disabling in-loop filtering mechanisms in conjunction with picture segmentation in video compression.

Terms such as "segment" or "picture segment" are used hereinafter in reference to any one or more macroblocks or equivalent (for example, treeblocks in WD4) that are smaller than the whole picture, and at whose boundaries at least one form of prediction is broken and/or at least one form of in-loop filtering is disabled. H.264-like Slices as well as WD4-like tiles, as described below (with tile_boundary_independence_idc equal to 1) are non-limiting examples of segments.

Figure 1:
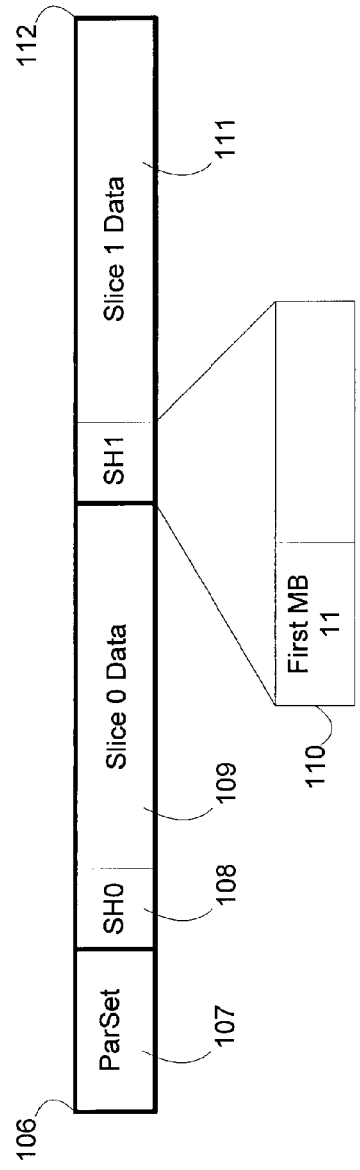
FIG. 1 is a diagram illustrating an exemplary picture having scan order slices, and a bitstream representing the coded picture in accordance with an embodiment of the invention.
Figure 2:
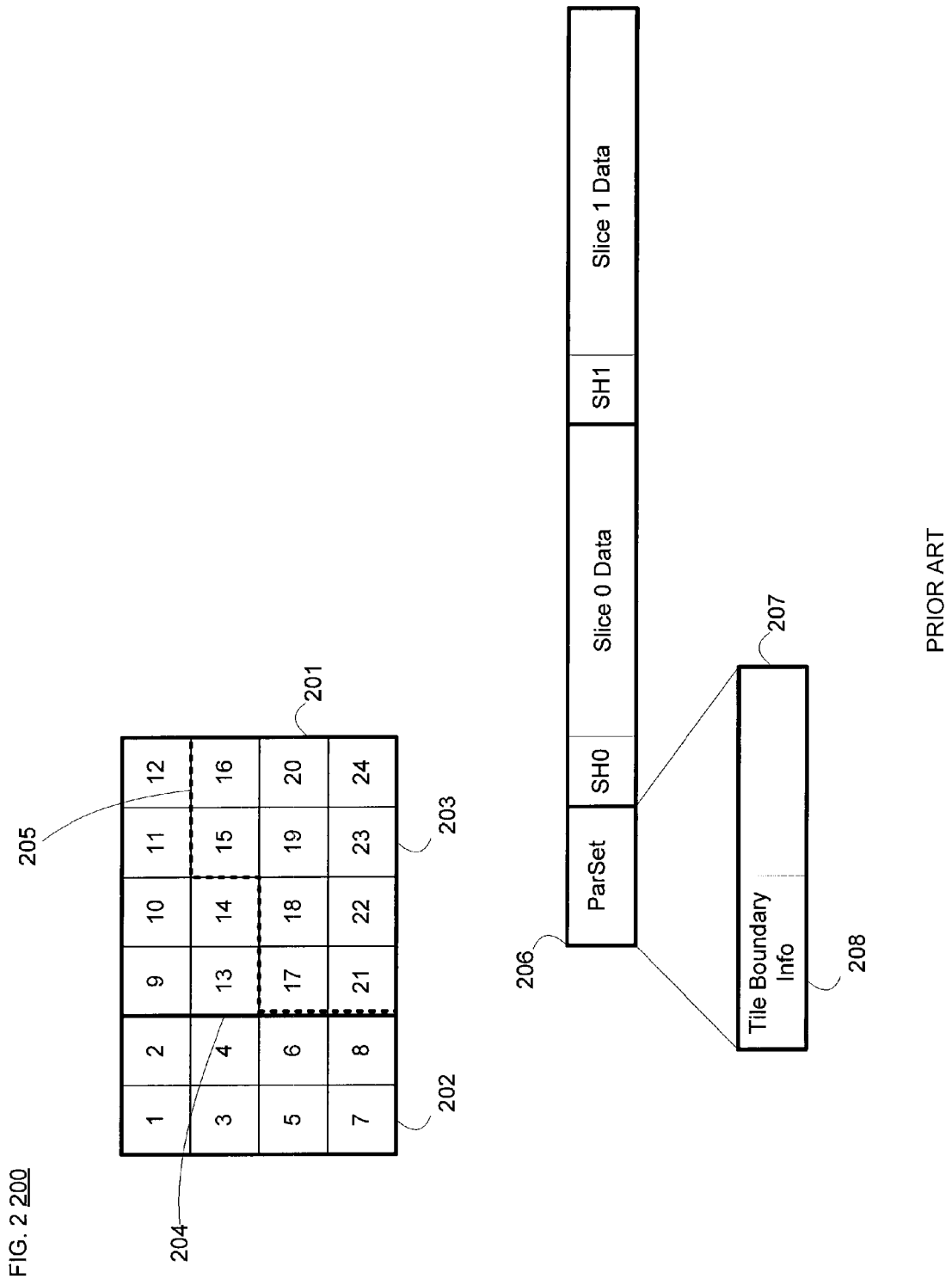
FIG. 2 is a diagram illustrating tiles and slices in accordance with an embodiment of the invention.
Figure 3:
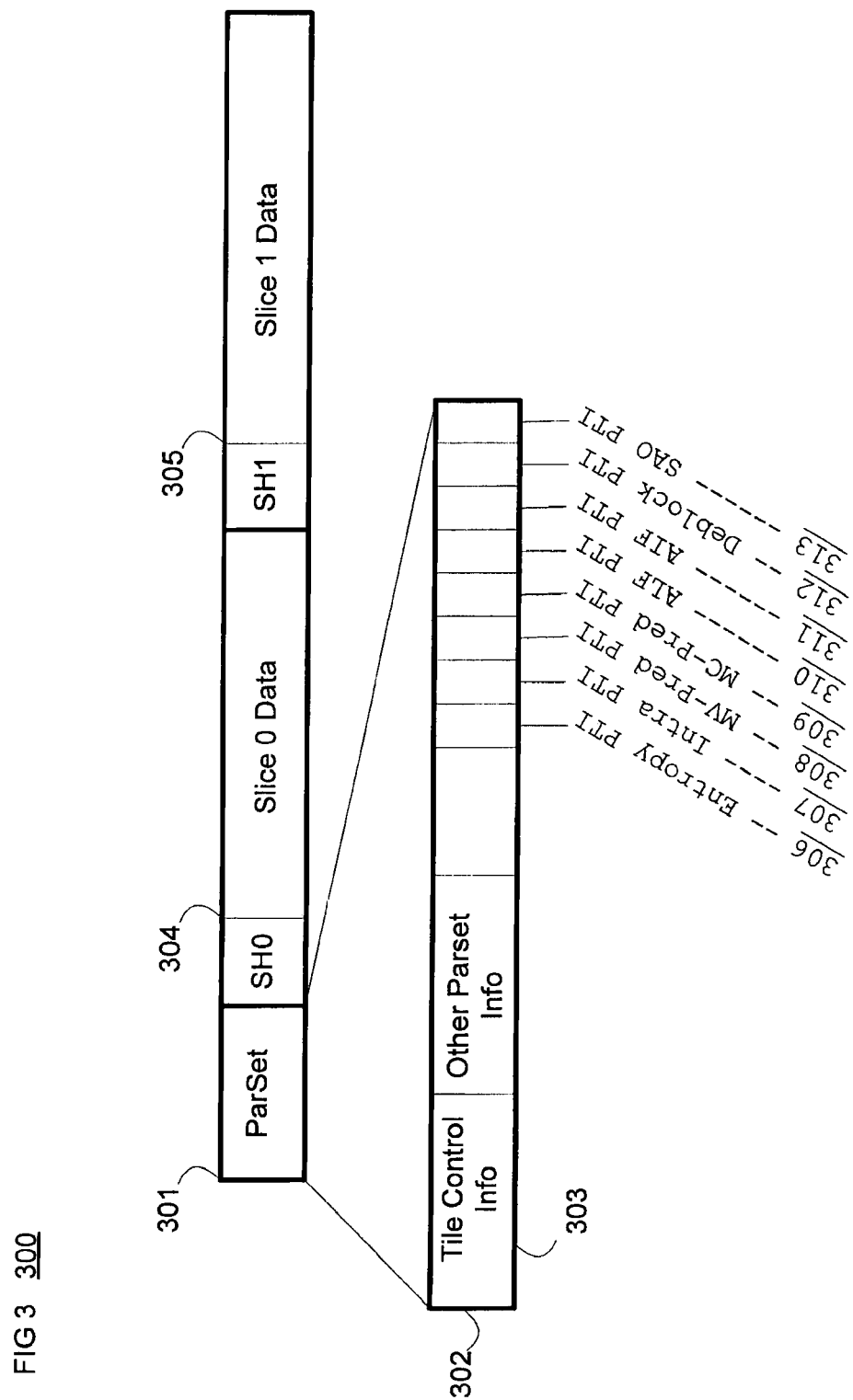
FIG. 3 is a block diagram illustrating a coded bitstream in accordance with an embodiment of the invention.
Figure 4:
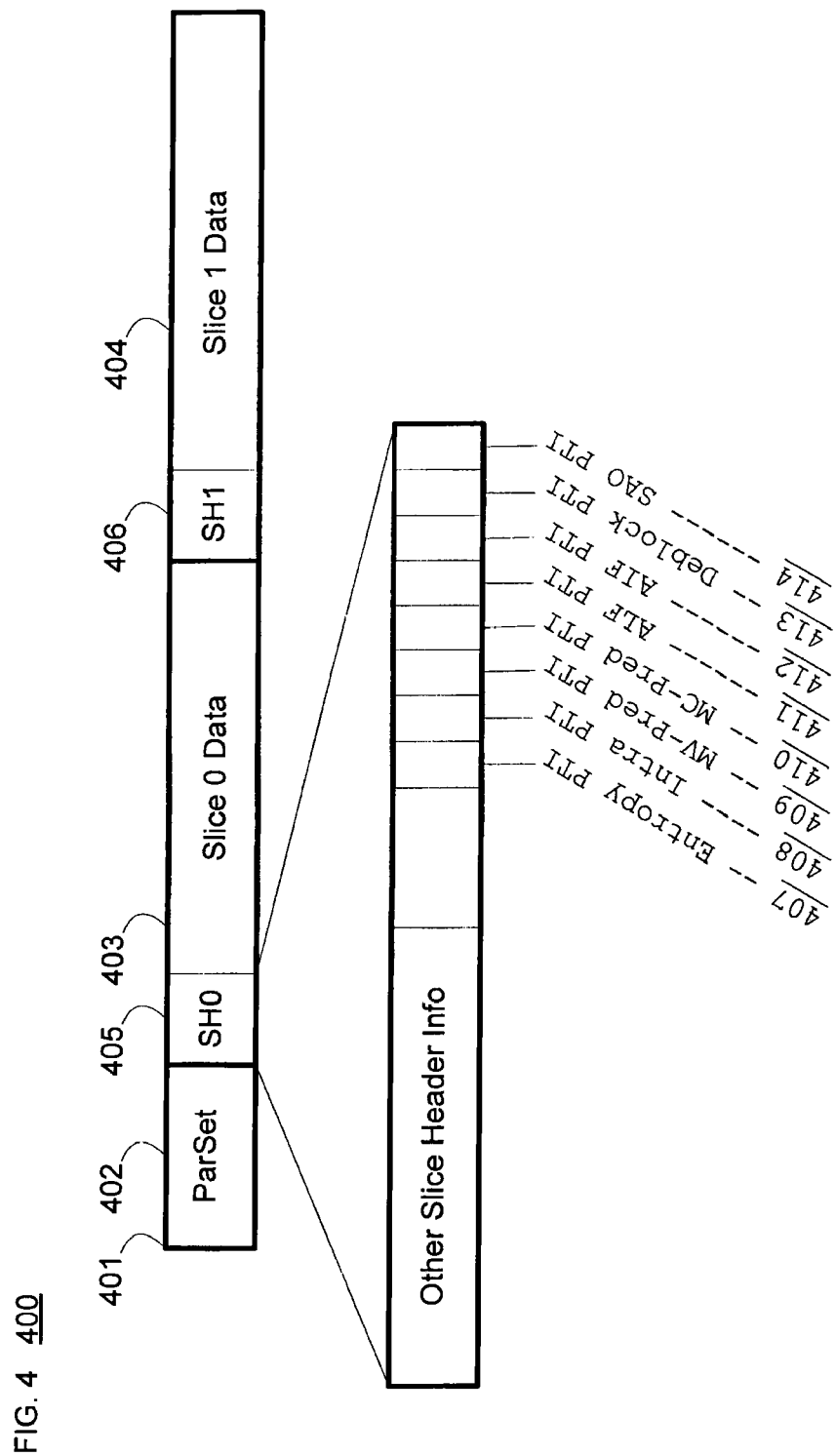
FIG. 4 is a block diagram illustrating a coded bitstream in accordance with an embodiment of the invention.
Figure 5:
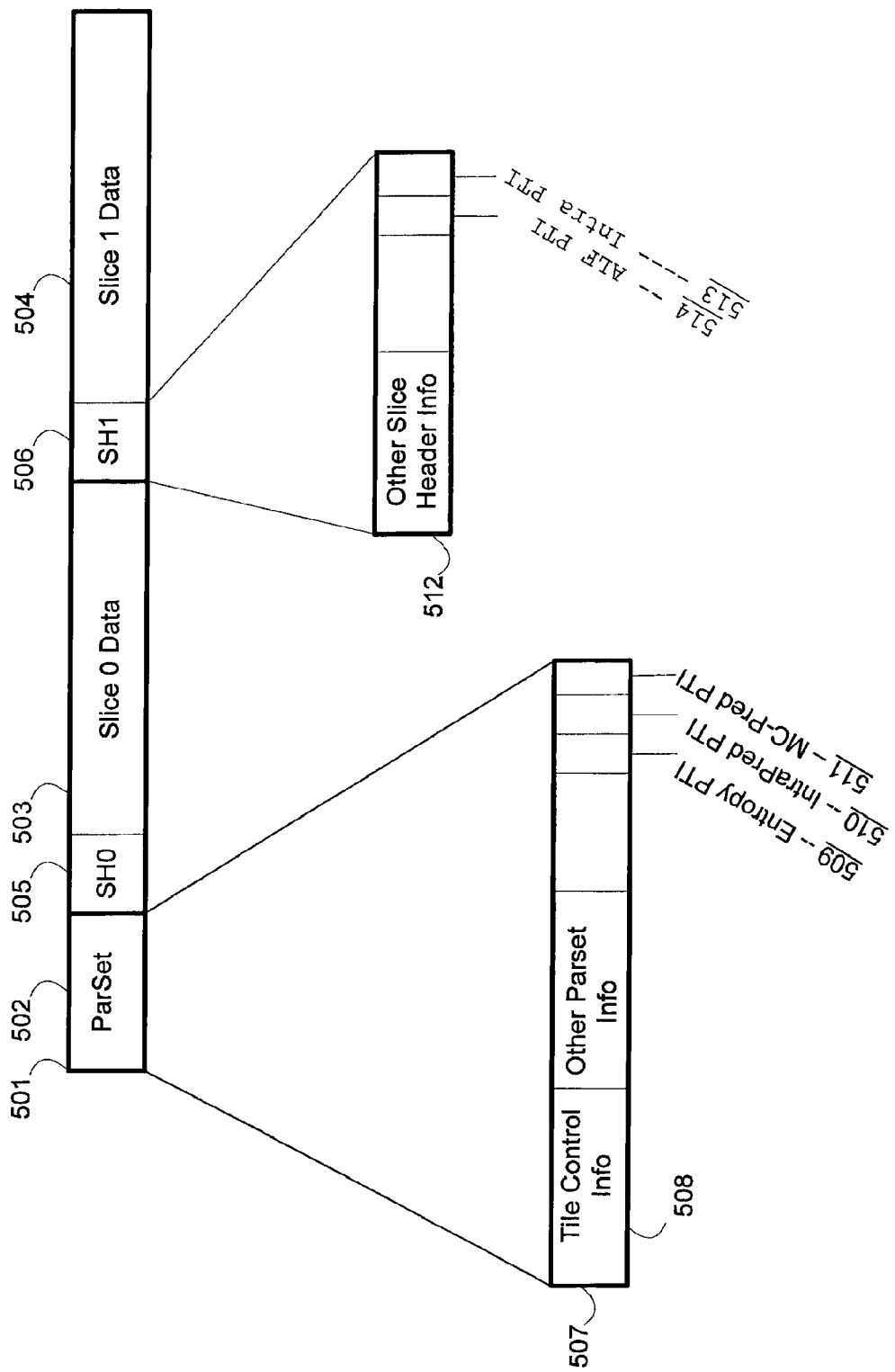
FIG. 5 is a block diagram illustrating a coded bitstream in accordance with an embodiment of the invention.
Figure 6:
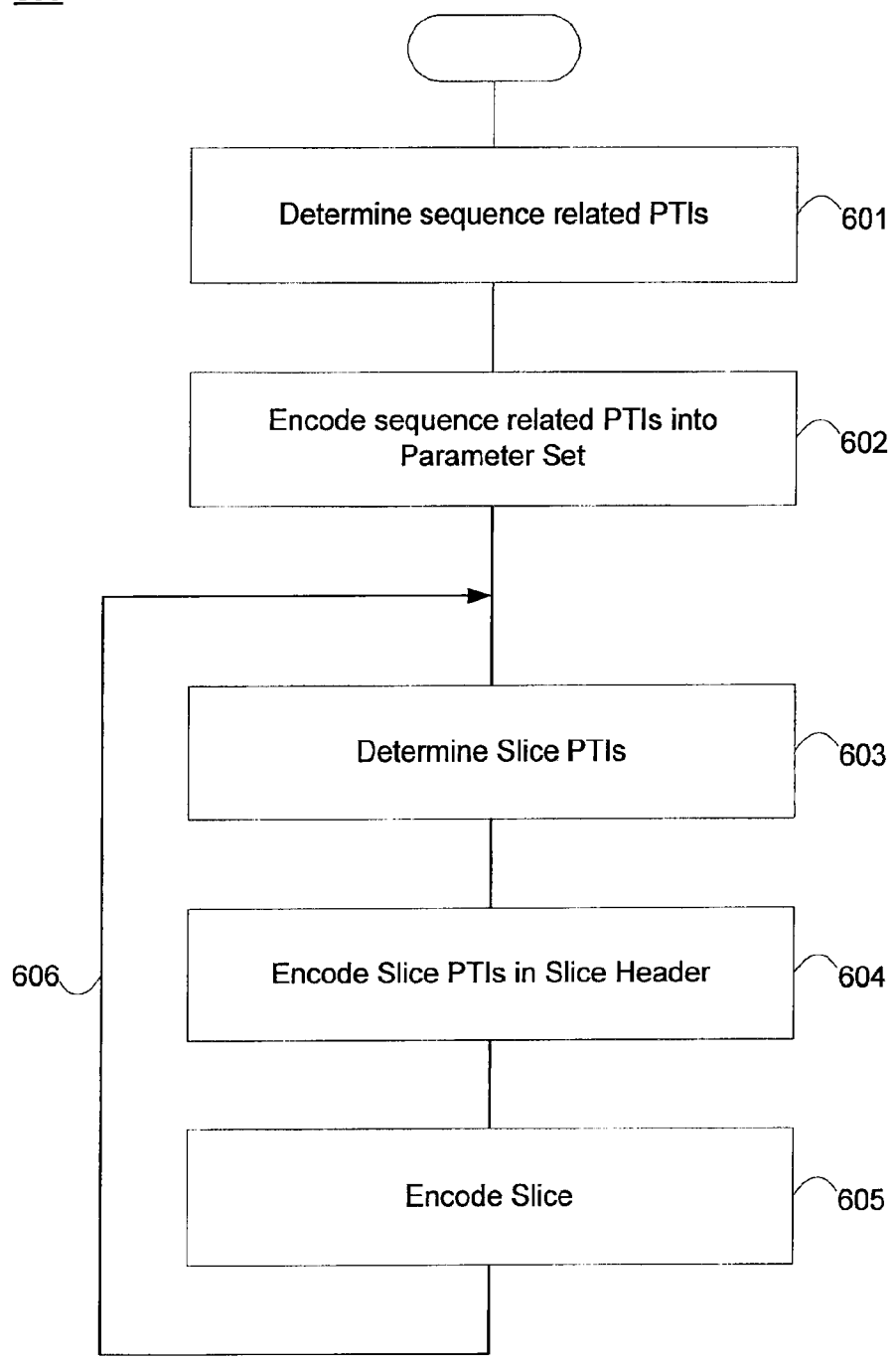
FIG. 6 is a flow diagram illustrating the operation of an exemplary decoder in accordance with an embodiment of the invention.
Figure 7:
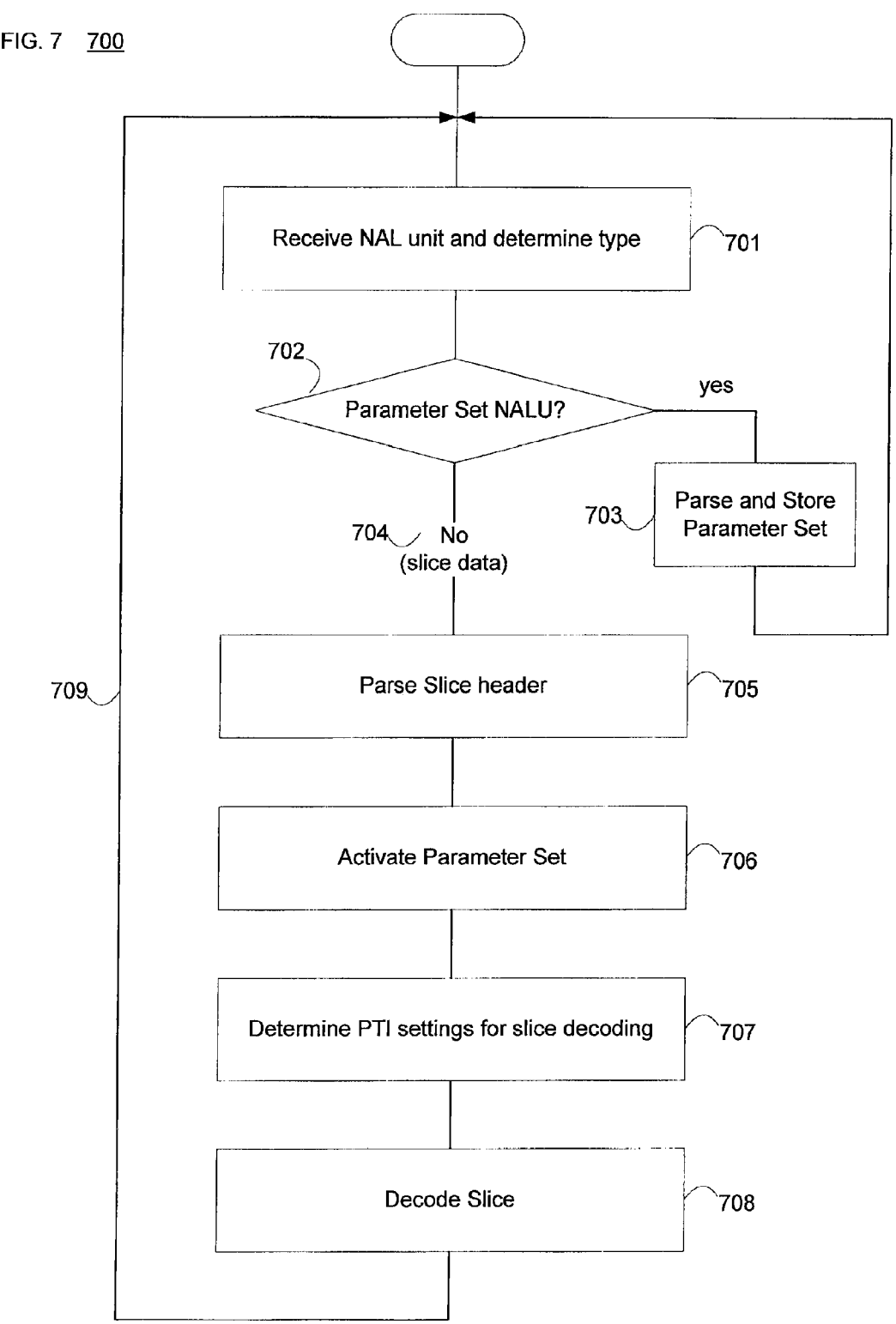
FIG. 7 is a flow diagram illustrating the operation of an exemplary decoder when decoding a slice in accordance with an embodiment of the invention; and, FIG. 8 is a block diagram illustrating a data processing system (e.g., a personal computer ("PC")) based implementation in accordance with an embodiment of the invention.
Figure 8:
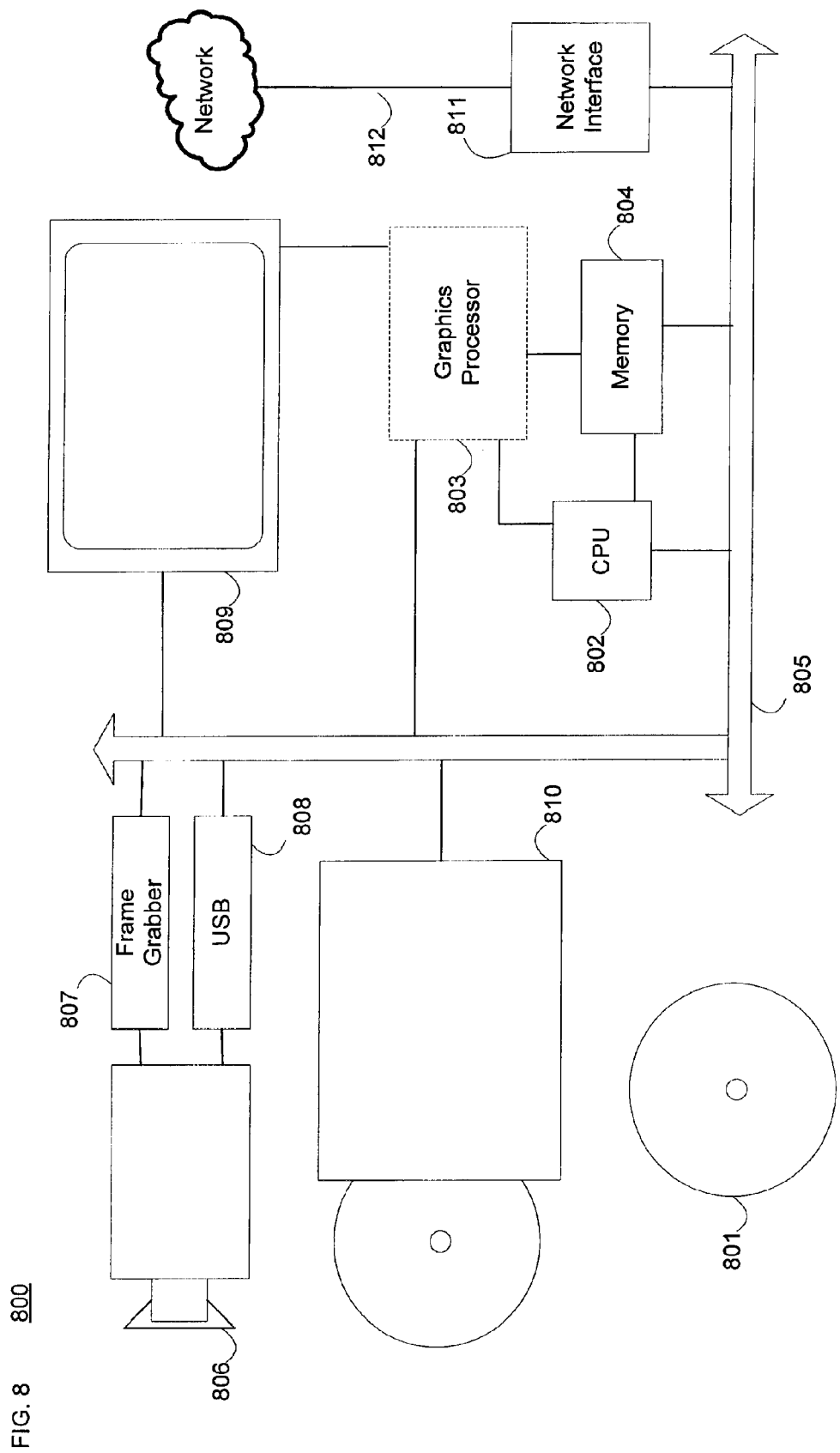

FIG. 2 shows an example 200, where a picture 201 is divided into two tiles 202, 203 by a vertical dividing tile boundary 204, depicted as a bold, solid line. Tiles can co-exist with slices within the picture 201. For example, the picture 201 is divided into two slices by the slice boundary 205 at the same time as being divided into the tiles 202, 203 by the tile boundary 204. Tiles (with tile_boundary_independence_idc equal to 1), as described in WD4, may in one or more respects generalize another type of picture segment, referred to as columns, which is described further in co-pending U.S. patent application Ser. No. 13/336,675, filed even date herewith, entitled "METHOD AND SYSTEM FOR PICTURE SEGMENTATION USING COLUMNS", the entire contents of which are incorporated herein by reference.

The bitstream 206 corresponding to transmission of the picture 201 can contain, for example, parameter sets 207 or other high-layer syntax elements that include tile boundary information 208 for identifying the tile boundary 204. The parts of the bitstream other than the parameter sets 207, however, do not include any information about tiles boundaries. A decoder can identify the tile to which a coded macroblock (also known as Largest Coding Unit (LCU) or (in WD4) treeblock) belongs by associating its internal state information of the macroblock currently being processed and the information of the tiles dimensions known from the parameter sets 207.

One difference between tiles and other rectangular picture segmentation mechanisms such as rectangular slices (a sub-mode of Annex K of ITU-T Rec. H.263) is that a tile (unlike the rectangular slices) does not require a header. The physical dimensions of a tile may be defined instead in the parameter set without inclusion of a header. In certain cases (with tile_boundary_independence_idc equal to 1), tile boundaries according to WD4 interrupt all in-picture prediction mechanisms, but allow for reference of samples in reference pictures that are not co-located with samples associated with the tile for which motion compensation is being performed. In addition, tile boundaries do not interrupt in-loop filtering, including the deblocking filter, sample adaptive offset filter, and adaptive loop filter.

However, it may also be convenient or desirable for an encoder or decoder to break a different set of prediction mechanisms using tiles. For example, at extremely high resolution, it can be advantageous to split the video pictures into tiles subject to requirements that motion vectors are not allowed to point outside of tile boundaries, and/or that a tile boundary is treated by encoder and decoder as a picture boundary (akin to H.263 annex R), or similar, thereby, for example, avoiding not only motion compensation across tile boundaries but also in-loop filtering.

In other cases, it may be convenient or desirable for the encoder or decoder to be able to handle full resolution video encoding except for the entropy coding of symbols. Such an encoder or decoder might, for example, involve dedicated signal processing hardware for sample based processing, but may use a general purpose multicore CPU for entropy coding and/or decoding, where a single core would not be able to handle the load (in HEVC, especially CABAC entropy coding is known to be computationally demanding). Accordingly, in order to support this use case, entropy coding may need to be broken at tile boundaries, while other in picture or inter picture prediction mechanisms may be capable of crossing slice and/or tile boundaries.

In still other cases, it may be convenient or desirable for the encoder or decoder to allow for limited cross-processor coordination across tile boundaries. In such cases, references to pixel values may not be possible, while reference to control information (such as the information necessary for motion vector prediction) may be available on the communication channel between the processors. In such a case, Intra prediction may not be possible, but motion vector prediction could be used.

There can be coding tools that are not directly related to prediction but still may advantageously be interrupted across slice or tile boundaries. For example, co-pending U.S. patent application Ser. No. 13/286,828, filed Nov. 1, 2011, entitled "ADAPTIVE INTERPOLATION IN DIGITAL VIDEO CODING", the entire contents of which are incorporated herein by reference, discloses an adaptive interpolation filter whose nature and coefficients can be encoder-selectable. It can be advantageous to limit the use of samples outside of a slice for interpolation filtering. Similarly, WD4 includes an adaptive interpolation filter, whose control is, at least in part, derived from certain pixels. It can be advantageous to limit this derivation to pixels only within the slice or tile boundary. It can also be advantageous to limit the filtering itself (in contrast to the derivation of filter control information) to pixels within the slice or tile boundaries. Also, WD4 includes other loop filters such as the adaptive loop filter (concerned with filtering all samples), a deblocking filter (concerned with filtering block boundaries) and a filtering mechanism known as sample-adaptive offset. These filters may all share properties similar to AIF. For example, in case of the adaptive loop filter, as specified in WD4, it can be advantageous to (possibly independently) disable access to information used to derive the filter taps across tile boundaries, as well as disable filtering across tile boundaries itself.

The boundaries of segments may be defined by picture (or higher) level syntax structures, such as, for example, parameter sets when using WD4 tiles, by segment header information (such as, for example, H.263 Annex K rectangular slices), by a combination of placement of a segment header in the bitstream and encoder/decoder state (such as, for example, H.264 slices when Flexible Macroblock Ordering (FMO) is not in use), or a combination of two or more of the aforementioned mechanisms (i.e., FMO defines slice groups, and the picture segment is defined within the slice group through a combination of slice header placements in the bitstream (identifying the first macroblock of the slice by its address) and implicit ascendance of macroblock addresses within the slice group until the end of the slice is detected through bitstream parsing or other means).

Described now are first mechanisms that allow the selection of prediction tools for tile boundaries, followed by mechanisms that allow the selection of prediction tools for slice boundaries. Finally, described is the interworking of the two mechanisms.

Referring to an example 300 in FIG.. 3, shown is a coded bitstream 301 comprising a parameter set 302 and two coded slices 304, 305. The coded slices 304, 305 may belong to one or two coded pictures. In WD4, a picture boundary can be identified by a slice header with an LCU address of 0. The parameter set 302 may include tile control information 303 (such as tile boundaries), and the information in the parameter set 302 is, in this example, assumed to pertain to both coded slices (i.e. the parameter set reference in the slice header contains the same index). In many WD4 and H.264 based systems, a parameter set pertains to tens, hundreds, or more slices.

According to an embodiment, the parameter set 302 may contain a plurality of prediction tool indication flags (PTIs). When the PTIs are set (i.e., enabled), for example, prediction across segment boundaries whichever encoding or decoding tool is associated with the flag may be allowed; otherwise when the PTIs are not set (i.e., disabled), such prediction may be forbidden. Flags may be defined, for example, for entropy coding prediction 306, intra prediction 307, motion vector prediction 308, motion compensated prediction 309, adaptive loop filtering 310, adaptive interpolation filtering 311, deblocking filtering 312, sample adaptive offset 313, and possibly other prediction and in-loop filtering tools defined in the video coding mechanism.

Including PTIs for individual prediction and in-loop filtering mechanisms, that pertain to all slices and pictures that reference the parameter set, may help to tailor the bitstream to the encoding and/or decoding environment, such as the hardware architecture of the encoder or decoder. Since the flags may be part of a parameter set, which may apply to many slices or pictures, the overhead of the PTIs in the parameter set may be negligible compared to the benefits they provide.

Referring to the example 400 depicted in FIG.. 4, shown is a coded bitstream 401 comprising a parameter set 402, and a coded picture containing two slices 403, 404. Each slice starts with a slice header 405, 406. Slice header 405 is enlarged to show parts of its information.

According to an embodiment, the slice header 405 may contain a plurality of prediction tool indication flags (PTIs). When one or more of the PTIs are set, for example, prediction and/or in-loop filtering across segment boundaries by whichever encoding or decoding tool is associated with the flag may be allowed; otherwise when the PTIs are not set, such prediction may be forbidden. PTIs may be defined, for example, for entropy prediction 407, intra prediction 408, motion vector prediction 409, motion compensated prediction 410, adaptive loop filtering 411, adaptive interpolation filtering 412, deblocking filtering 413, sample adaptive offset 414, and possibly other prediction and in-loop filtering tools defined in the video coding mechanism.

Including PTIs for individual prediction and in-loop filtering mechanisms that pertain to a given slice, can help to adapt the bitstream to the content, thereby improving coding efficiency.

Described now is how the two mechanisms described above can interact.

Referring to an example 500 shown in FIG.. 5, shown is a coded bitstream 501 containing a parameter set 502 and two slices 503, 504, each starting with a corresponding slice header 505, 506.

Parameter set 502, which is shown enlarged at 507, for example, includes tile control information 508 or other information related to header-less segment boundaries that, for example, could indicate a vertical tile boundary 204 as shown in FIG.. 2. Further, the parameter set 502 may contain one or more PTIs. Shown here are three PTIs, one associated with entropy prediction 509, one with intra prediction 510, and one with motion compensation 511. These flags may control the decoder prediction at the tile boundary 204. The tile boundary 204 may, for example, be set by the tile control information 508 such that the picture 201 is divided vertically into two tiles 202, 203. The mechanism described here may also work with other arrangements of tile boundaries, including a combination of vertical and horizontal boundaries.

The coded picture may, for example, also contain two coded slices 503, 504, each starting with a corresponding slice header 505, 506. As shown in FIG.. 2, the (uncoded) slices corresponding to coded slices 503, 504 may, for example, encompass the spatial area of macroblock addresses 1 through 14, and 15 through 24, respectively. Slice header 506 is shown enlarged at 512 and may contain a plurality of PTIs. Shown are two PTIs, one associated with intra prediction 513, the other with adaptive loop filtering (ALF) 514. However, it is noted that there may be, but is no requirement for, an overlap between the PTIs of the parameter set 502 or the slice header 506.

According to an embodiment, the PTIs 509, 510, 511 of the parameter set 502 control the prediction and in-loop filtering across the tile boundary 204 as defined by the tile control information 508.

According to an embodiment, the PTIs 513, 514 of the slice header 512 control the prediction and in-loop filtering across the boundaries between the slices 503, 504. For example, the slice boundaries of slice 504 have one boundary other than the picture boundary, which is marked by the dashed boldface slice boundary line 205.

As a result, in the example 200, some prediction and in-loop filter mechanisms are interrupted by tile boundaries (so to enable distribution of the picture coding effort among several processors), while other prediction and in-loop filter mechanisms are interrupted selectively, and under control of the slice header 506, at slice boundaries (thereby giving the encoder full control over prediction and in-loop filtering mechanisms being broken, so to be able to select any particular combination of prediction and in-loop filtering mechanisms for the content being coded, included combinations that may be desirable or convenient for a given application or use).

If a PTI pertaining to the same prediction or in-loop filtering mechanism is present in both parameter set 502 and in a slice header 506, and in the situation where the corresponding tile and slice boundaries are aligned, at least two decoder reactions may be possible. Such choices may be made statically specified in the standard, through a profile/level selection, or dynamically based on control information in a parameter set or other high layer syntax elements.

One choice is that the PTIs in the parameter set 502 overwrite contradictive information in the slice header 506. This choice may have the advantage of providing a decoder with certainty that it can distribute segments to various processors or cores, without having to implement mechanisms that would allow for sharing information between those segments.

Another choice is that the PTIs in the slice header 508 overwrite contradictive information in the parameter set 502. This choice may allow for greater encoder flexibility in choosing its tools. Still other reactions may be possible as well.

In order to optimize the encoding of the flags (be they located in slice header 508 or parameter set 502), in some cases, it may be beneficial to specify in a standard any of the following:

(1) some PTIs may not be part of a parameter set or slice header if a certain profile and/or level is indicated, as the prediction or in-loop filtering tool is not available in this profile/level.

(2) two or more PTIs may be "bundled" into a single combination PTI, if, for example in a certain profile, it is determined that the flexibility of switching on/off those individual PTIs independently is unnecessary or even undesirable.

(3) in some cases, a PTI may not best be coded as a Boolean (i.e. binary) parameter. For example, the need for cross processor coordination in case of motion compensation may be determined at least in part by the length of the motion vector pointing outside the co-located spatial area covered by the slice or tile. Accordingly, in an embodiment, PTI information may also be coded as an integer or other non-boolean parameter, thereby to indicate suitable ranges of values for prediction, such as the maximum length of a motion vector pointing outside of a segment boundary.

(4) in some cases, PTI values may not need to be physically present in the bitstream, as their values can be derived from other properties of the bitstream. For example, an Intra slice may not need to contain a PTI related to motion compensation, because motion compensation may, by design of the standard, not occur in an intra slice.

Described now is the operation of an encoder that, according to embodiments, may be suitable for use with any of the conFIG.urations of PTI information previously described.

Referring to FIG.. 6, in an embodiment, an encoder may operate according to flowchart 600. Before encoding a first slice of a video sequence, the encoder may determine (601) the sequence-related settings for PTIs as well as a tile layout of the video pictures in the video sequence. This determination may take into account the hardware architecture of the encoder, the hardware architecture of a decoder, a possible tile layout suggested or dictated by the hardware architectures, knowledge about a transmission network (if any), such as the MTU size, and so on. In some cases, PTI values may be mandated by a system-level standard, which can be taken into account in the determination by the encoder. For example, a future digital TV standard may conceivably require that a certain tile layout and certain PTI settings controlling prediction and in-loop filtering across tile boundaries be used for certain (high) resolutions, so to enable cost efficient multi-processor/multicore implementations. It is possible that only a subset of all PTIs need to be fixed at sequence level.

Several options for those settings have already described before.

After the determination, the encoder may encode (602) the sequence-related PTIs into an appropriate high level syntax structure, such as a sequence or picture parameter set, sequence, GOP, or picture header. The encoder may also have the option (through the syntax structure of the video coding standard) to leave PTI(s) undefined during this encoding.

The sequence-related PTIs may stay constant at least for one full video picture (unless overwritten by slice header based PTIs, as described later), but, in many cases, may stay constant for at least one "sequence" (for example, all pictures between two IDR pictures and the leading IDR picture in the video stream), and perhaps during an entire video encoding session. For example, the sequence-related PTIs may at least partly driven by hardware constraints, which are unlikely to change during a session. Henceforth assumed for convenience is this latter case.

The encoder continues by encoding slices. In order to do so, the encoder can determine (603) slice-level PTIs, which may interact with sequence-related PTIs, as already described. The slice-level PTIs can be encoded (604) as part of the encoding of the slice header.

The slice can then be encoded (605) according to whichever coding standard is being applied, such as WD4 or H.264, while taking into account the breaking of prediction and/or in-loop filtering mechanisms across both slice and tile boundaries as indicated by the PTIs.

The encoding continues (606) with the next slice.

Described now is the operation of a decoder that, according to embodiments, may be suitable for use with any of the conFIG.urations of PTI information previously described.

FIG.. 7 is a flowchart 700 of a decoder that may be used in an embodiment of the invention. The decoder may receive (701) a NAL unit from the bitstream and determine its type. If the NAL unit type is indicative of a parameter set (702), the decoder may perform parameter set parsing and storage (703) in accordance with the video coding standard employed. (Other high level syntax structures, such as sequence, GOP, or picture headers may also be used for this purpose.).

If the NAL unit type is indicative of slice data (704) (other cases not depicted) the decoder may parse the slice header (705) and then respond in accordance with the information, such as PTI information, coded therein. For example, the slice header may contain a parameter set reference, and this parameter set may be "activated" (706) as described in the video coding standard—that is, the values of the parameter set with the reference indicated become valid. As PTIs may be part of the parameter set, through the activation (706), their values may become valid as well.

The slice header may further include its own PTIs, as already described, which may be different from the PTIs included in the parameter set. Options for how to arbitrate between PTI information coded into the slice header and PTI information coded into the parameter set have already been described. For example, by correlating the slice header based PTIs (if present) with the parameter set header PTIs (if present), and taking into account any restrictions that may be present in other parts of the video coding standards (such as restrictions and/or default settings of PTIs by profiles and levels), the decoder may determine (707) the final PTI settings to be used in decoding the subject slice. It is noted that PTIs may be different for different borders of the slice, depending on the PTI settings of the parameter set and the PTI settings of the slice header, including the particular case of when a slice boundary is aligned with a tile boundary.

Taking the final PTI settings into account, the decoder may decode (708) the slice using prediction and/or in-loop filtering techniques across slice or tile boundaries as indicated by the information coded into the PTIs.

The process continues (709) with the next NAL unit.

Not shown in FIG.. 7 is the processing of NAL units other than slice or parameter set NAL units.

FIG.. 8 is a block diagram illustrating a data processing system (e.g., a personal computer ("PC")) 800 based implementation in accordance with an embodiment of the invention. Up to this point, for convenience, the description has not related explicitly to possible physical implementations of the encoder and/or decoder in detail. Many different physical implementations based on combinations of software and/or components are possible. For example, in some embodiments, the video encoder(s) and/or decoder(s) may be implemented using custom or gate array integrated circuits, in many cases, for reasons related to cost efficiency and/or power consumption efficiency.

Additionally, software based implementations are possible using general purpose processing architectures, an example of which is the data processing system 800. For example, using a personal computer or similar device (e.g., set-top-box, laptop, mobile device), such an implementation strategy may be possible as described in the following. As shown in FIG.. 8, according to the described embodiments, the encoder and/or the decoder for a PC or similar device 800 may be provided in the form of a computer-readable media 801 (e.g., CD-ROM, semiconductor-ROM, memory stick) containing instructions conFIG.ured to enable a processor 802, alone or in combination with accelerator hardware (e.g., graphics processor) 803, in conjunction with memory 804 coupled to the processor 802 and/or the accelerator hardware 803 to perform the encoding or decoding. The processor 802, memory 804, and accelerator hardware 803 may be coupled to a bus 805 that can be used to deliver the bitstream and the uncompressed video to/from the aforementioned devices. Depending on the application, peripherals for the input/output of the bitstream or the uncompressed video may be coupled to the bus 805. For example, a camera 806 may be attached through a suitable interface, such as a frame grabber 807 or a USB link 808, to the bus 805 for real-time input of uncompressed video. A similar interface can be used for uncompressed video storage devices such as VTRs. Uncompressed video may be output through a display device such as a computer monitor or a TV screen 809. A DVD RW drive or equivalent (e.g., CD ROM, CD-RW Blue Ray, memory stick) 810 may be used to input and/or output the bitstream. Finally, for real-time transmission over a network 812, a network interface 811 can be used to convey the bitstream and/or uncompressed video, depending on the capacity of the access link to the network 812, and the network 812 itself.

According to various embodiments, the above described method(s) may be implemented by a respective software module. According to other embodiments, the above described method(s) may be implemented by a respective hardware module. According to still other embodiments, the above described method(s) may be implemented by a combination of software and/or hardware modules.

While the embodiments have, for convenience, been described primarily with reference to an example method, the apparatus discussed above with reference to a data processing system 800 may, according to the described embodiments, be programmed so as to enable the practice of the described method(s). Moreover, an article of manufacture for use with a data processing system 800, such as a pre-recorded storage device or other similar computer readable medium or product including program instructions recorded thereon, may direct the data processing system 800 so as to facilitate the practice of the described method(s). It is understood that such apparatus and articles of manufacture, in addition to the described methods, all fall within the scope of the described embodiments.

In particular, the sequences of instructions which when executed cause the method described herein to be performed by the data processing system 800 can be contained in a data carrier product according to one embodiment of the invention. This data carrier product can be loaded into and run by the data processing system 800. In addition, the sequences of instructions which when executed cause the method described herein to be performed by the data processing system 800 can be contained in a computer program or software product according to one embodiment of the invention. This computer program or software product can be loaded into and run by the data processing system 800. Moreover, the sequences of instructions which when executed cause the method described herein to be performed by the data processing system 800 can be contained in an integrated circuit product (e.g., a hardware module or modules) which may include a coprocessor or memory according to one embodiment of the invention. This integrated circuit product can be installed in the data processing system 800.

The above embodiments may contribute to an improved system and method for selectively breaking prediction and/or in-loop filtering in video coding and may provide one or more advantages. For example, including PTIs for individual prediction and/or in-loop filtering mechanisms, that pertain to all slices and pictures that reference the parameter set, may help to tailor the bitstream to the encoding and/or decoding environment, such as the hardware architecture of the encoder or decoder. Further, including PTIs for individual prediction and/or in-loop filtering mechanisms that pertain to a given slice, can help to adapt the bitstream to the content, thereby improving coding efficiency.

The embodiments of the invention described herein are intended to be exemplary only. Accordingly, various alterations and/or modifications of detail may be made to these embodiments, all of which come within the scope of the invention.

What is claimed is:

1. A method for decoding by a decoder a coded video picture, the method comprising:
   obtaining a first slice and a second slice of the coded video picture,
   wherein the first slice and the second slice are divided by at least one slice boundary,
   wherein at least the first slice is divided by a tile boundary to belong to two tiles, and
   wherein the two tiles do not have associated tile headers;
   obtaining, from the coded video picture, a parameter set including a first flag for controlling a sample adaptive offset operation across the tile boundary;
   determining whether to apply the sample adaptive offset operation across the tile boundary according to the first flag;
   obtaining, from the coded video picture, a slice header including a second flag for controlling a sample adaptive offset operation across the at least one slice boundary; and
   determining whether to apply the sample adaptive offset operation across the at least one slice boundary according to the second flag.

2. The method of claim 1, wherein the second slice is spatially encompassed within a single tile of the coded video picture.

3. The method of claim 1, wherein the sample adaptive offset operation across the at least one slice boundary is disabled across the at least one slice boundary in response to the second flag, and the sample adaptive offset operation across the tile boundary is enabled in response to the first flag.

4. The method of claim 1, wherein determining whether to apply the sample adaptive offset operation across the tile boundary according to the first flag comprises:
   determining that the parameter set includes the first flag; and
   in response to determining that the parameter set includes the first flag, applying the sample adaptive offset operation across the tile boundary.

5. The method of claim 1, wherein determining whether to apply the sample adaptive offset operation across the tile boundary according to the first flag comprises:
   determining that the parameter set includes the first flag; and
   in response to determining that the parameter set includes the first flag, disabling the sample adaptive offset operation across the tile boundary.

6. The method of claim 1, wherein determining whether to apply the sample adaptive offset operation across the at least one slice boundary according to the second flag comprises:
   determining that the slice header includes the second flag; and
   in response to determining that the slice header includes the second flag, applying the sample adaptive offset operation across the at least one slice boundary.

7. The method of claim 1, wherein determining whether to apply the sample adaptive offset operation across the at least one slice boundary according to the second flag comprises:
   determining that the slice header includes the second flag; and
   in response to determining that the slice header includes the second flag, disabling the sample adaptive offset operation across the at least one slice boundary.

8. The method of claim 1, wherein the slice header is associated with the first slice and a different slice header is associated with the second slice.

9. The method of claim 1, wherein the parameter set is a picture parameter set.

10. The method of claim 1, wherein the parameter set is a sequence parameter set.

11. A non-transitory computer-readable medium having instructions stored thereon which, when executed by one or more processors, cause the one or more processors to perform operations comprising:
    obtaining a first slice and a second slice of a coded video picture,
    wherein the first slice and the second slice are divided by at least one slice boundary,
    wherein at least the first slice is divided by a tile boundary to belong to two tiles, and
    wherein the two tiles do not have tile headers;
    obtaining, from the coded video picture, a parameter set including a first flag for controlling a sample adaptive offset operation across the tile boundary;
    determining whether to apply the sample adaptive offset operation across the tile boundary according to the first flag;
    obtaining, from the coded video picture, a slice header including a second flag for controlling a sample adaptive offset operation across the at least one slice boundary; and
    determining whether to apply the sample adaptive offset operation across the at least one slice boundary according to the second flag.

12. The computer-readable medium of claim 11, wherein the second slice is spatially encompassed within a single tile of the coded video picture.

13. The computer-readable medium of claim 11, wherein the sample adaptive offset operation across the at least one slice boundary is disabled across the at least one slice boundary in response to the second flag, and the sample adaptive offset operation across the tile boundary is enabled in response to the first flag.

14. A decoder, comprising:
    one or more processors; and
    a storage medium coupled to the one or more processors having instructions stored thereon which, when executed by the one or more processors, cause the one or more processors to perform operations comprising:
    obtaining a first slice and a second slice of a coded video picture,
    wherein the first slice and the second slice are divided by at least one slice boundary,
    wherein at least the first slice is divided by a tile boundary to belong to two tiles, and
    wherein the two tiles do not have tile headers;
    obtaining, from the coded video picture, a parameter set including a first flag for controlling a sample adaptive offset operation across the tile boundary;
    determining whether to apply the sample adaptive offset operation across the tile boundary according to the first flag;
    obtaining, from the coded video picture, a slice header including a second flag for controlling a sample adaptive offset operation across the at least one slice boundary; and
    determining whether to apply the sample adaptive offset operation across the at least one slice boundary according to the second flag.

15. The decoder of claim 14, wherein the second slice is spatially encompassed within a single tile of the coded video picture.

16. The decoder of claim 14, wherein the sample adaptive offset operation across the at least one slice boundary is disabled across the at least one slice boundary in response to the second flag, and the sample adaptive offset operation across the tile boundary is enabled in response to the first flag.

* * * * *